(12) United States Patent
Egnelöv et al.

(10) Patent No.: US 6,264,673 B1
(45) Date of Patent: Jul. 24, 2001

(54) DEVICE FOR PERFORMING HEMOSTASIS

(75) Inventors: Per Egnelöv; Dan Akerfeldt, both of Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 09/424,337

(22) PCT Filed: May 20, 1998

(86) PCT No.: PCT/SE98/00957

§ 371 Date: Nov. 22, 1999

§ 102(e) Date: Nov. 22, 1999

(87) PCT Pub. No.: WO98/52477

PCT Pub. Date: Nov. 26, 1998

(30) Foreign Application Priority Data

May 23, 1997  (SE) .................................................. 9701935

(51) Int. Cl.$^7$ .................................................. A61B 17/00
(52) U.S. Cl. .......................... 606/201; 606/215; 128/887
(58) Field of Search .................................. 606/201, 202, 606/203, 215, 216; 602/53; 128/887

(56) References Cited

U.S. PATENT DOCUMENTS

| 3,884,240 | | 5/1975 | Gilman | 128/325 |
| 4,760,846 | * | 8/1988 | Kelly et al. | 606/201 |
| 5,269,803 | * | 12/1993 | Geary et al. | 606/201 |
| 5,307,811 | | 5/1994 | Sigwart et al. | 128/677 |
| 5,512,056 | * | 4/1996 | Stevens et al. | 606/203 |
| 5,542,427 | | 8/1996 | Akerfeldt | 128/677 |
| 5,601,597 | * | 2/1997 | Arrowood et al. | 606/203 |
| 5,690,610 | * | 11/1997 | Ito et al. | 602/53 |
| 5,728,120 | * | 3/1998 | Shani et al. | 606/201 |

FOREIGN PATENT DOCUMENTS 0 462 088 A2  12/1991  (EP).

OTHER PUBLICATIONS

"Clinical use and Practical tips" RADI publication 60020 Rev. 02. 990125 (16 pp.).

* cited by examiner

*Primary Examiner*—Gary Jackson
(74) *Attorney, Agent, or Firm*—Foley & Lardner

(57) ABSTRACT

The invention relates to a device for performing hemostasis at two symmetrically located puncture sites in the femoral arteries or veins of a patient. It comprises a beam member (6, 8) provided with two attachment devices (10, 12) for pressure pads. There are belts for securing the device to the patient to provide a pressure on the puncture sites, and means (18, 20, 24, 26) for adjusting the distance between said attachment. The invention also provides a method of controlled hemostasis at two puncture sites in each femoral artery or vein of a patient after catheterization, comprising providing a beam member having two pressure pads, adapted to bear against each puncture site, adjusting the center-to-center distance of said pressure pads by moving at least one of said pressure pads along said beam member, applying said pressure pads at said puncture sites, securing said beam member carrying said pressure pads to the body of said patient, by tightening a belt around the body.

16 Claims, 5 Drawing Sheets

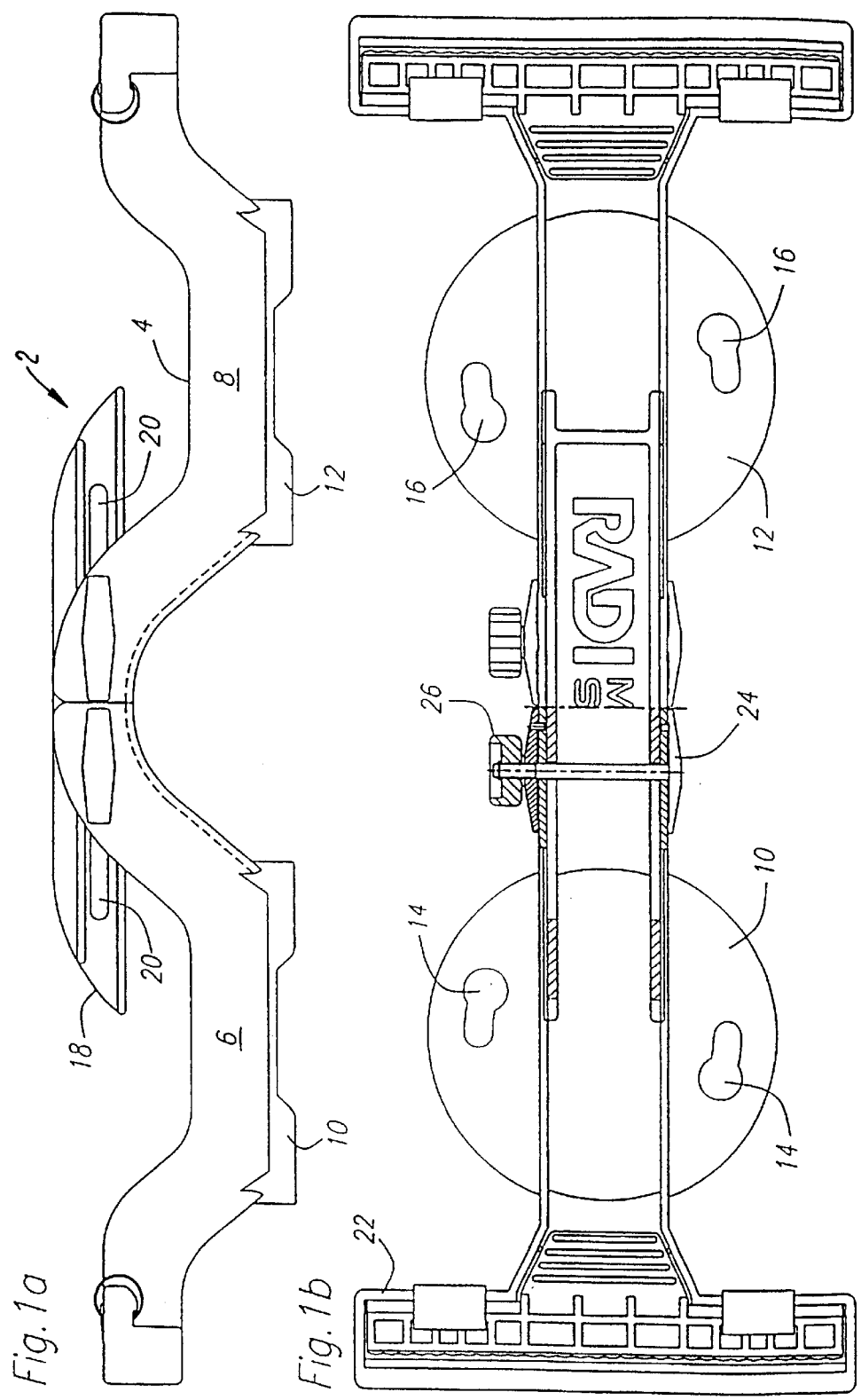

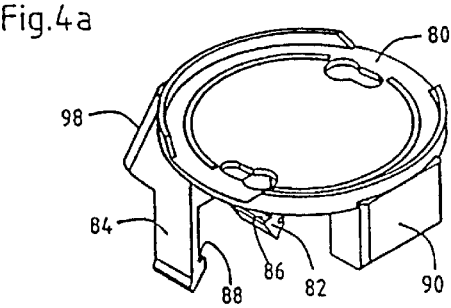
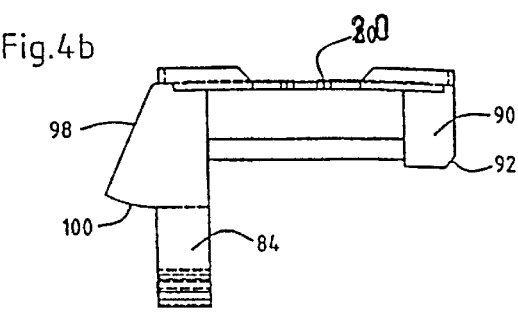
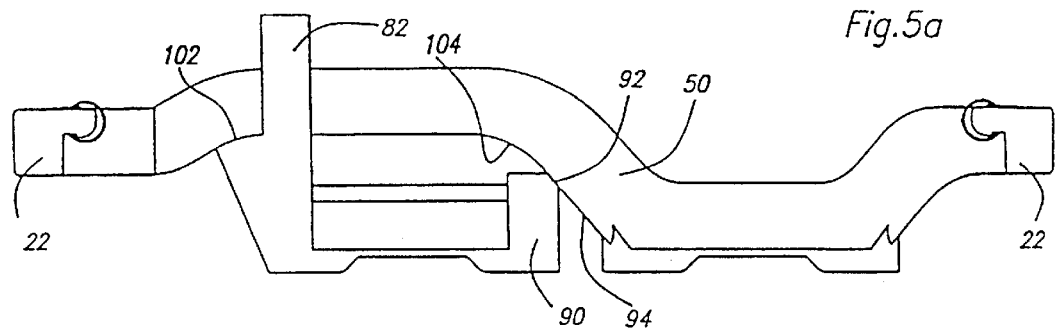
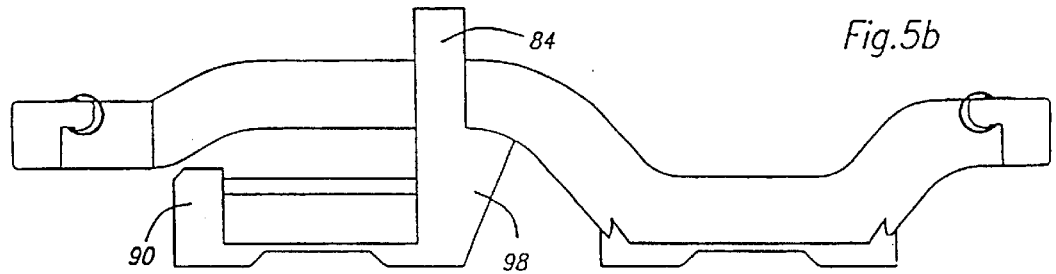
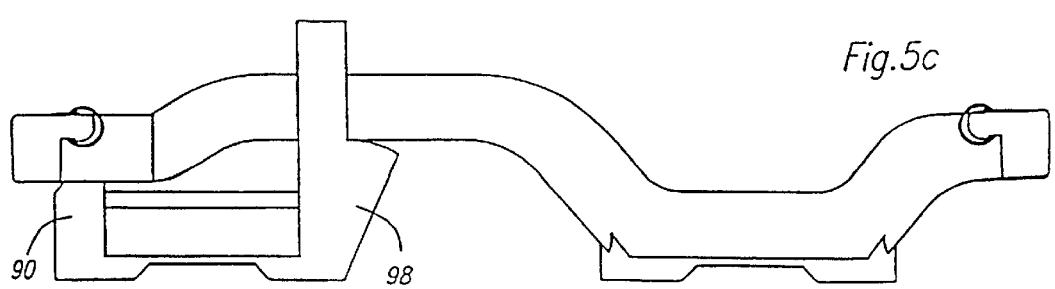

DEVICE FOR PERFORMING HEMOSTASIS

The present invention relates in general to hemostasis, and in particular to hemostasis of the femoral arteries or veins.

Specifically it relates to a device for performing hemostasis and to to a method of hemostasis.

BACKGROUND OF THE INVENTION AND RELATED ART

Hemostasis of i.a. the femoral artery is performed after e.g. catheterization in order to prevent bleeding. A device for facilitating such hemostasis is disclosed in EP-0 462 088 (Radi Medical). The object of the device disclosed in said patent is to provide a controlled and directional pressure against the puncture in the femoral artery, by means of an inflatable pressure pad attached to an asymmetric arc or beam member, secured with a strap or belt extending around the body of the patient.

In certain circumstances it may be desirable to enter both the right and left side femoral arteries and veins of both sides of the body.

It has been tried to use two devices of the type disclosed in the above mentioned patent for hemostasis of two punctures. However, it has turned out that such an approach is difficult to master, because the stability of the two devices will be severely impaired, and it will also be inconvenient for the patient.

Another solution has been to use one device of the mentioned type for one puncture, combined with manual compression of the other puncture.

The latter approach is labor intensive and inconvenient for both patient and medical staff.

SUMMARY OF THE INVENTION

The invention seeks to provide a device that overcomes the above mentioned problems with the prior art device.

The problem is solved by providing a femoral compression device for performing hemostasis at two symmetrically located puncture sites in the femoral arteries, comprising a beam member provided with two attachment means for disposable pressure pads, and means for adjusting the distance between said attachment means to correspond to the distance between said puncture sites such that said pressure pads accurately bear against said puncture sites at essentially right angles with respect to the body surface. The invention is defined in claim 1.

According to the invention there is also provided a method of controlled hemostasis at two puncture sites, as defined in claim 15.

In one embodiment the device comprises two beam halves connected to an adjustment means for providing a variable center-to-center distance.

In another embodiment there is provided a separate attachment device for variable attachment on one leg of a beam having one integral attachment means.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will become more fully understood from the detailed description given hereinbelow and the accompanying drawings which are given by way of illustration only, and thus not limitative of the present invention, and wherein FIG. 1a is a side view of a first embodiment of the invention;

FIG. 1b is a top view with portions broken away of the device in FIG. 1a;

FIG. 2b is a top view of the device of FIG. 2a;

FIG. 3b is a top view of the device of FIG. 3a;

FIG. 4a is a perspective view of another embodiment of an adapter;

FIG. 4b is a side view of the device of FIG. 4a;

FIG. 5a illustrates one way of positioning the device of FIG. 4 on a femoral compression beam;

FIG. 5b illustrates another way of positioning the device of FIG. 4 on a femoral compression beam;

FIG. 5c illustrates another way of positioning the device of FIG. 4 on a femoral compression beam;

DETAILED DESCRIPTION OF PREFERRED EMBODIMENTS

Figure 2A:
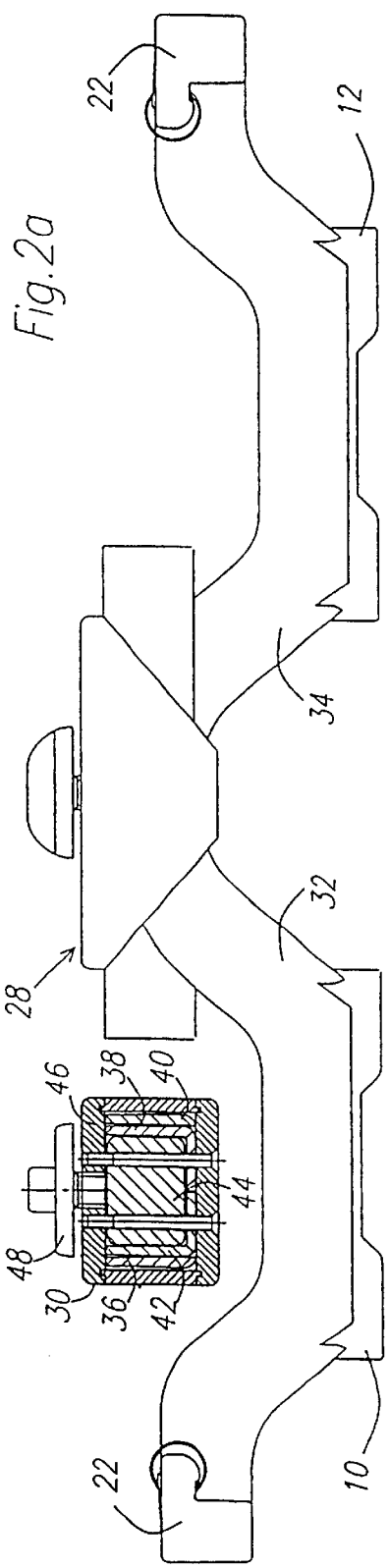
FIG. 2a is a side view of a second embodiment of the invention.

FIG. 1a is a side view of a first embodiment of the compression device, generally identified with reference numeral 2, according to the invention, and FIG. 1b is a top view of the device in FIG. 1a with a portion broken away.

The shown compression device 2 comprises an overall beam or arch structure 4, having a generally "U"-shaped cross section (the "U" opening upwards as seen in FIG. 1a), and comprising two beam halves 6, 8. The beam and the entire assembly has a generally linear configuration, i.e. it extends generally in one plane. Each beam half is provided with an integrally formed attachment means 10 and 12 respectively, for attaching inflatable, preferably disposable, pressure pads (not shown) to the beam structure 4.

These pressure pads will in operative position bear against punctures in the femoral arteries on both sides of the body. These punctures will be located such that they lie essentially in the same plane, i.e. on the "upper" side of the body, when the patient lies on his back. Thus, the pressure pads are also located essentially in the same plane, and the forces from said pads acting on the punctures will be essentially parallel to each other and directed from above. The downward forces will be at essentially right angles with respect to the plane in which the punctures are located.

In one end said beam halves are provided with means 22 for attaching a belt or strap (not shown) for tightening the device around a patient's body.

The attachment means 10, 12 comprises snap fit means in the form of recesses 14, 16 respectively mating with corresponding pins on the pressure pads. Of course other means of attaching said pressure pads are conceivable, e.g. VELCRO® type means, double adhesive tape, threads etc., and the method of attachment does not form part of the invention.

The two beam halves 6, 8 are displaceable relative to each other in order to enable a center-to-center distance between the attachment means, and thereby to adjust the device to fit a particular distance between puncture sites to which simultaneous compression is to be applied. It should be noted that the beam halves are thus movable in relation to each other in the same linear direction, and thereby the distance between the lines of force acting on the respective puncture will also change. The displacement is achieved by providing an adjustment member 18, comprising an elongated element having a longitudinally extending recess 20 formed therein. The adjustment member 18 fits in the interior of the beam profile. At the end of each beam half opposite the strap attaching means 22 there is provided a "T"-screw 24 extending through the beam and through the recess 20 of said adjustment member 18. Thus, the screw acts as a guide member for enabling a sliding movement of each beam half in said recess 20 along the 25 adjustment member 18. A tightening nut 26 is provided such as to enable fixing each beam half at a desire position along the adjustment member 18. In the position where the center-to-center distance is the shortest, the free ends of the beam halves 6, 8 contact each other.

In FIG. 2a a second embodiment of the invention is shown.

In this embodiment there is also provided an adjustment member 28. However, in this case the adjustment member is designed as a housing 30, adapted to receive the free ends of each respective beam half 32, 34. The free ends, i.e. the ends opposite the ends provided with the strap attachments 22, are extended in comparison with the free ends of the embodiment of FIGS. 1a–b.

Figure 2B:
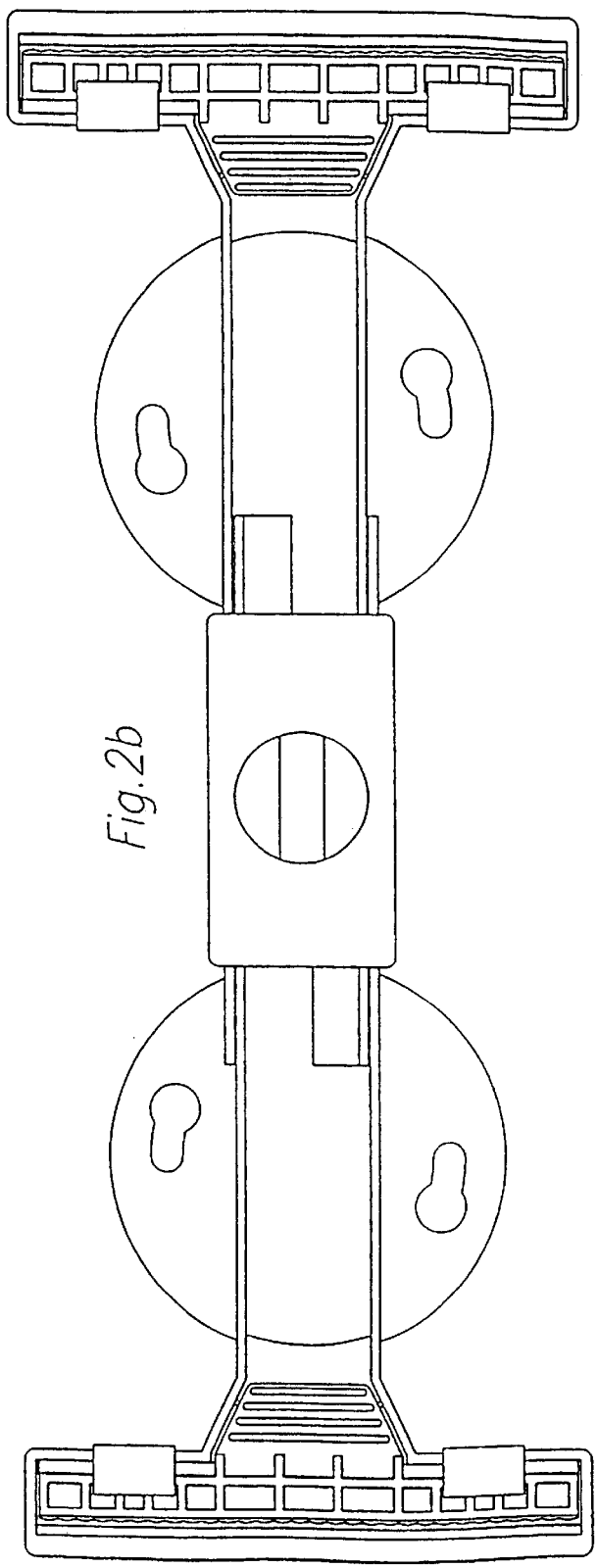
Figure 3C:
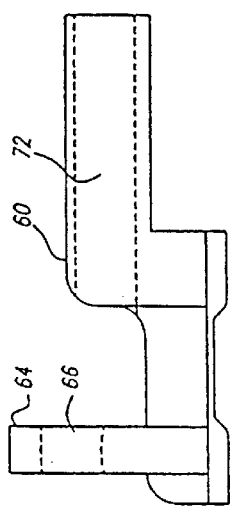
FIG. 3c is a side view of an adapter.
Figure 3D:
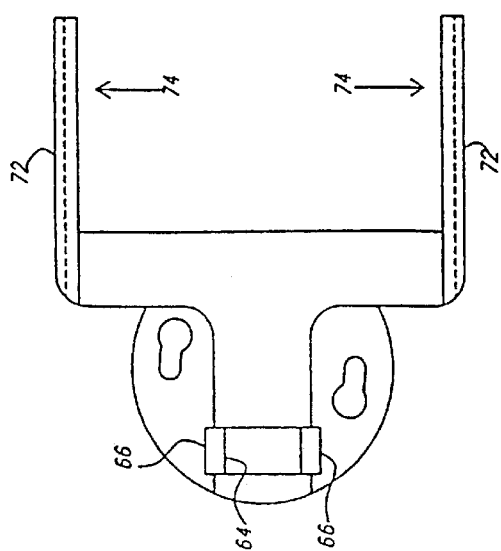
FIG. 3d is a top view of the adapter of FIG. 3c.
Figure 3A:
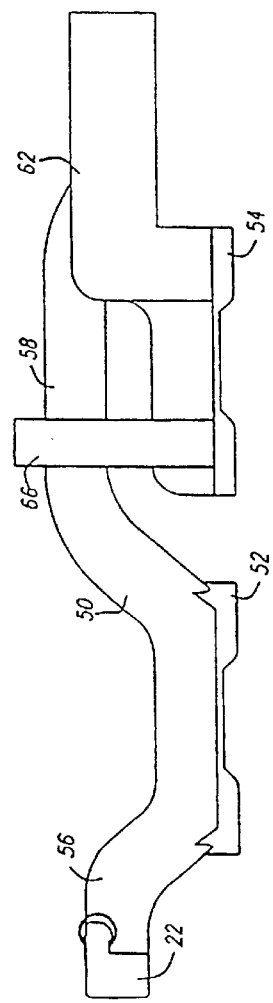
FIG. 3a is a side view of a third embodiment of the invention, comprising a femoral compression beam with an adapter.
Figure 3B:
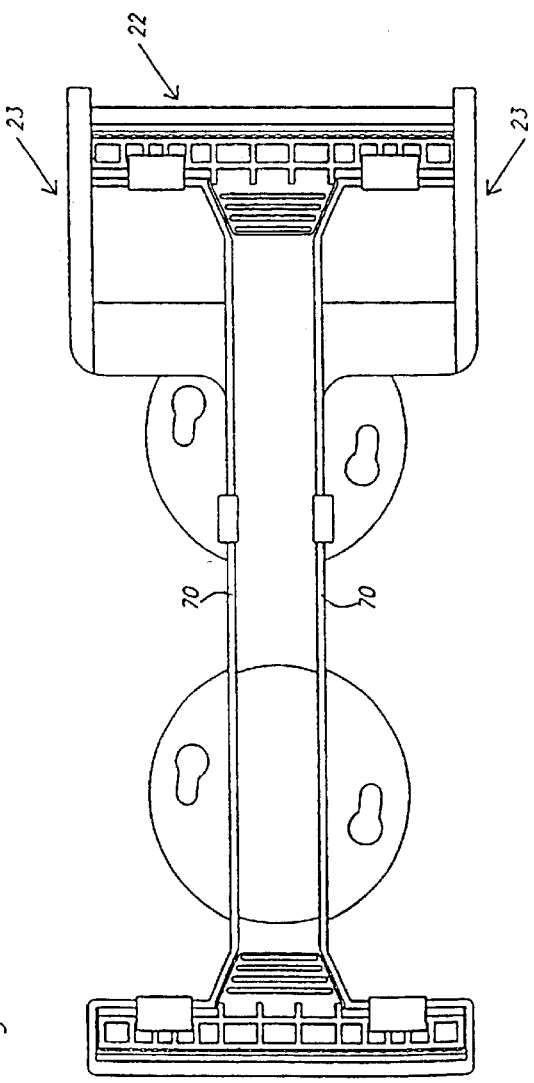

Furthermore, said free ends are designed so as to be slideable inside each other. This is achieved by removing material from the bottom portion of the "U"-shaped profile of each beam half, to one side thereof, such that a recess is formed matching the bottom portion of the other beam half not having material removed. This is clear from FIG. 2b wherein the wall portion 36 and the bottom portion 38 belongs to the right hand beam half 34 of FIG. 2a, and the wall portion 40 and the bottom portion 42 belongs to the left hand beam half 32 in FIG. 2a.

Inside the adjustment member 28 there is provided a piston member having a width and height such that it fills the space remaining inside the housing when said free ends of the respective beam halves are inserted in the adjustment member 28. In the top portion 46 of the housing 30 there is provided a screw 48 which when tightened acts on the piston 44 to clamp the free ends of the beam halves located inside said housing 30 of the adjustment member 28. In this way the beam halves are independently adjustable in terms of their positions, and thereby the center-to-center distance of the attachment means 10, 12 is also adjustable.

The free ends of the beam halves may have other configurations as long as they are movable inside said adjustment member 28.

Thus, it is conceivable to provide the respective free ends with mutually engaging means, such as teeth, that will effectively lock the beam halves to each other. The tightening means could also have other designs, such as a lever type device of some resilient material.

Turning now to FIGS. 3a–d a third embodiment of the invention is illustrated.

In this embodiment the adjustability of the center-to-center distance of the attachment means, is achieved by providing a beam structure 50 having a first attachment means 52 integral with the beam structure, and a second attachment means 54 provided on a separate item, below referred to as an adapter 60, connectable at a desired position on said beam structure 50. In this case the beam structure is asymmetric with respect to beam portions extending from the first attachment 52, i.e. a first beam portion 56 is shorter than a second beam portion 58. Each beam portion is provided with a belt attaching means 22 of the same type as in the other embodiments.

The adapter 60 comprises a connector structure 62 having an essentially T-shaped base portion 68, on the bottom side of which a pressure pad attachment means 54 is mounted. The connector structure 62 is provided with means for securing it to the longer beam portion 58 of the beam structure 50 in the form of latch or hook means 64 provided on two parallel legs 66 extending vertically from the upper side of the base portion 68 of the connector structure 62. In the shown embodiment the beam structure 50 has a generally "U"-shaped cross section, thus having vertical side walls 70 forming engagement sites mating with said latch or hook means 64.

The connector structure further comprises two horizontal, flat legs 72, having their wide dimension in the vertical direction. These legs are adapted to engage with the outermost edge portions 23 of the belt attachment means 22 provided on said longer extension 58 of the beam structure 50. This guiding function is provided by the presence of recesses 74 provided on the inner sides of the legs 72.

Thus, when the adapter 60 is to be positioned on the beam structure 50 at a desired site corresponding to the desired center-to-center distance of the pressure pad attachments 52, 54, the legs 74 are brought over said edge portion 23, which fits in said recesses 74, and then the legs 66 are pushed over the side walls 70 of the beam portion 58 such that the latches 64 snaps around the edge of the side walls 70. In order to further secure the adapter at the desired location, there may be provided a further locking means (not shown), in the form of a loop hinged on one leg, and adapted to be brought across the other leg. By selecting the material of the entire structure to be at least somewhat resilient, the "springy" property of the material will contribute to retain the adapter in a fixed position.

In FIGS. 4 and 5 there is shown a fourth embodiment of the invention, which is a variant of the third embodiment.

Turning now to FIGS. 4a and b, which is a perspective view and a side view respectively of another embodiment of the adapter. It comprises one attachment means 80 for a, preferably disposable, pressure pad. From said attachment means, at the periphery thereof, two vertical legs 82, 84 extend in a vertical direction. The legs have a design similar to that of the legs described in connection with the third embodiment. Thus, the legs are provided with latches or hooks 86, 88 adapted to engage with the side walls of the beam structure of a femoral compression device.

At the periphery of the attachment means, opposite to where the legs are provided, there is a support member 90 mounted. It extends in the same vertical direction as the legs 82, 84, and is adapted to rest against the upper surface of the beam structure, thereby providing stability to the adapter means. In order to provide this supporting function in all positions, the support member 90 is beveled 92 at one edge, in order to accommodate the sloping surface 94 of the beam in one position of the adapter (se further below).

As can be seen from the Figures, this embodiment may be positioned on the beam in two orientations, one (FIG. 5a) providing a rather short center-to-center distance, and a second orientation (FIG. 5b–c) providing a range of center-to-center distances.

In order to provide adequate support for the adapter against the beam, there is provided a widening portion 98 on the legs and extending between the legs, and having a lower curved surface 100 with the same radius of curvature as the curved portions 102, 104 of the beam structure. When the legs have been snap fitted on the beam, this widened portion 98 rests against the beam at said curved beam portion. Thus, in the extreme positions of the adapter (FIG. 5a and c respectively), this widened extension of the legs thereby provides the desired support. Also the previously mentioned support member 90 in practically all positions rests against the beam, at least when the belt has been tightened, and thereby two points of support are obtained for the adapter, which insures adequate stability in use.

This embodiment is suitable for use together with a commercially available femoral compression device, obtainable from Radi Medical Systems, under the trade name FEMOSTOP.

The above disclosed embodiments have been shown with a beam member having strap attaching means 22 provided on extensions of said beam member. Although this is a preferred way of securing the belt from a stability and patient comfort point of view, it is conceivable to arrange the strap in other ways. One alternative way is shown in FIGS. 6a and 6b.

Figure 6A:
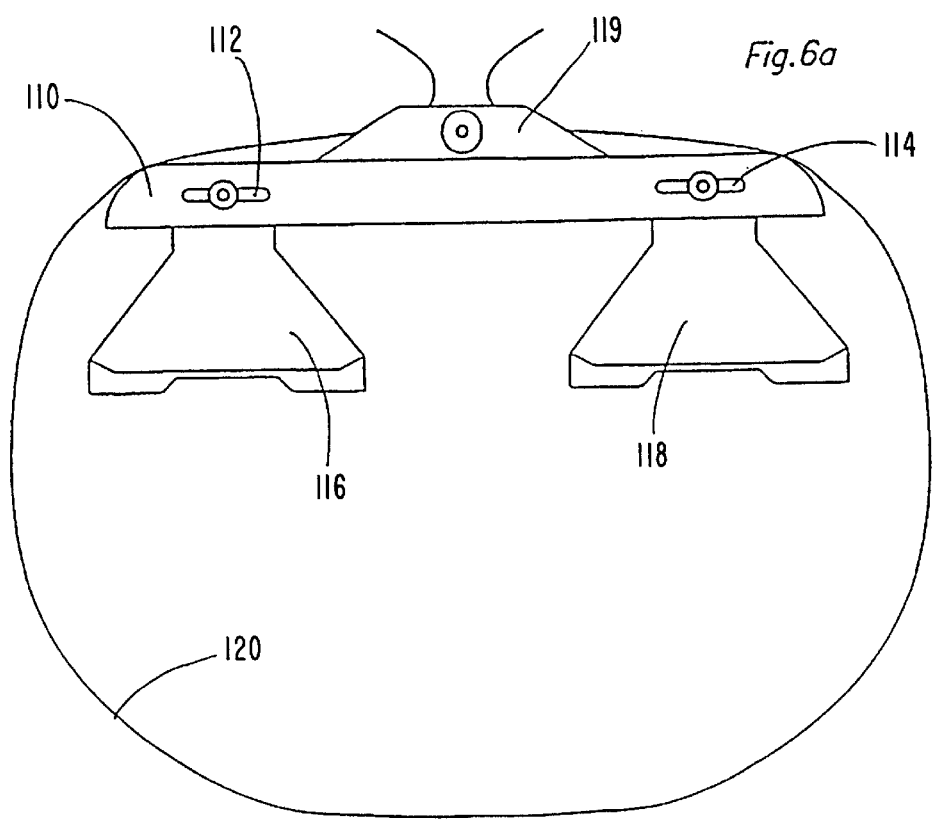
FIG. 6a shows a first alternative design of the strap attaching means.

In FIG. 6a there is disclosed a device comprising a beam member 110 having two recesses 112, 114 in which pressure pad attachment means 116, 118 respectively are slidably mounted. A bolt and nut is use for securing said attachments in a desired position in said recesses, on the top surface of the beam 110 there is provided a suitable strap attaching means 119 for fixing a strap 120 around the body of a patient. The strap attaching means may be of any suitable design, and does not form part of the invention per se.

Figure 6B:
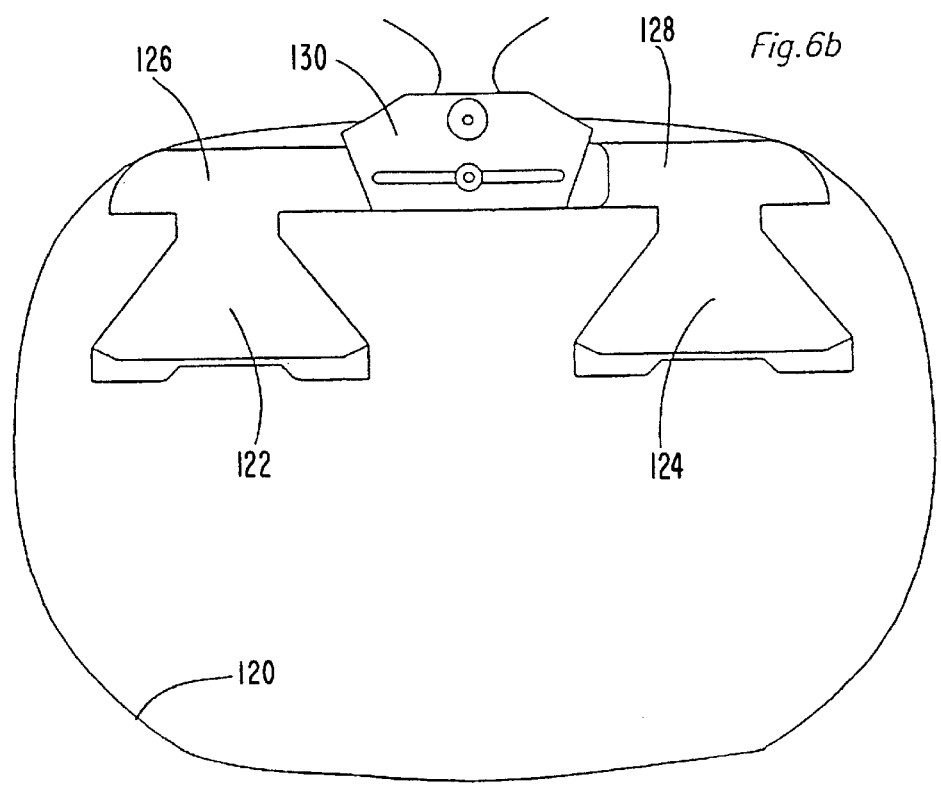
FIG. 6b shows a second alternative design of the strap attaching means.

In FIG. 6b an alternative design is disclosed. Here the pressure pad attachment means 122, 124 respectively are integral with one beam half 126, 128 respectively. Said beam halves 126, 128 are slideable inside each other, e.g. in the same way as disclosed in connection with FIG. 2. A strap attaching means 130 is formed as a housings similar to the embodiment of FIG. 2, in which the beam halves are insertable. This member is thus integral with the strap attaching means 130.

The method of performing a controlled hemostasis according to the invention will now be described.

After catheterization of a patient through the femoral arteries or veins, bleeding has to be suppressed. This is achieved by providing a device according to the invention as disclosed above. Two pressure pads, preferably of a disposable type, are attached to the beam on the attachment means provided on the beam structure.

The center-to-center distance between said pressure pads is adjusted to correspond to the distance between puncture sites on the arteries/veins.

The device is placed over the patient such that the pads rest against the puncture sites. If needed, further adjustment of said center-to-center distance is made. A belt or strap secured in the strap attaching means provided on the beam is tightened around the patient's body. The pressure is maintained for a time sufficient to effectively stop bleeding, whereupon the pressure is released by loosening the strap, and removing the device.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A device for performing hemostasis at two symmetrically located puncture sites in the femoral artery or veins of a patient, comprising
    a beam member (6, 8; 32, 34; 50; 110; 126, 128);
    two attachement means (10, 12; 52, 54; 116, 118; 122, 124) for attaching pressure pads, provided on said beam member;
    means for securing the device to a patient to provide a pressure on the puncture sites;
    characterized in that
    the attachment means are located essentially in the same plane; and in that
    there are provided means for adjusting the distance between said attachment means along said beam member (6, 8; 32, 34; 50; 110; 126, 128) to correspond to the distance between the puncture sites such that the pressure pads accurately bear against the puncture sites, at essentially right angles with respect to the plane in which the punctures are located, and such that the forces acting on each respective puncture site are essentially parallel to each other.

2. The device of claim 1, wherein said beam member (6, 8; 32, 34) is provided with attachment means (10, 12) integral with said beam member for securing two pressure pads thereon.

3. The device of claim 2, wherein said beam member comprises two halves (6, 8), each carrying one attachment means (10, 12), and connected to each other by a distance adjustment member (18; 28) providing for said variable distance.

4. The device of claim 3, wherein said distance adjustment member is an elongated element (18) comprising a recessed portion (20), and wherein each beam half comprises a protruding element (24) mating with said recess such that each beam half is slideable in and along said recess, and wherein each beam half is provided with tightening means (24, 26) for fixing thereof at a selected position in said recess.

5. The device of claim 4, wherein said tightening members comprise a screw and nut (24, 26), said screw also forming said protruding element.

6. The device of claim 3, wherein said distance adjustment member (28) comprises a beam receiving compartment, in which a free end of each said beam half is insertable, said free ends being adapted to fit inside each other in a sliding relationship, said distance adjustment member (28) being provided with tightening means (48, 44) for securing said beam halves in a selected position in said beam receiving space.

7. The device of claim 1, wherein one of said attachment means (52) is integral with said beam member (50), and one attachment means (54) is provided on a separate item (60) connectable at a selectable position on said beam member (50).

8. The device of claim 7, wherein said beam member (50) is asymmetric in that one portion thereof extending from said integral attachment means is longer than the other portion, said beam comprising elongated fastening means (70) extending along said beam, and wherein said separate item comprises locking means (64, 66) mating with said fastening means to insure a secure attachment of said separate item.

9. The device of claim 8, wherein said beam has an arc shape and wherein said separate item comprises positioning means mating with selected portions of said arc shaped beam, such that the separate attachment means is secured in a fixed position on said beam when said locking means engage said fastening means.

10. Adapter means, usable as a separate attachment device for a pressure pad on an asymmetric femoral compression device as claimed in claim 7, with one integral attachment means for a pressure pad, said adapter comprising an attachment means (54; 80) for a pressure pad, and means (64, 66, 68, 72; 84, 88, 98) for attaching the adapter at a selected position on said femoral compression device, such as to provided a second attachment means for a pressure pad on said femoral compression device, to render it usable for treating two punctures at one time.

11. The adapter as claimed in claim 10, comprising a connector structure (62) having an essentially T-shaped base portion (68), on the bottom side of which said pressure pad attachment means (54) is mounted, said connector structure (62) being provided with means in the form of latch or hook means (64) provided on two parallel legs (66) extending vertically from the upper side of the base portion (68) of the connector structure (62) for securing it to the beam structure (50).

12. The adapter as claimed in claim 11, wherein the connector structure further comprises two horizontal, flat legs (72), having their wide dimension in the vertical direction, and adapted to engage with the outermost edge portions (23) of belt attachment means (22) provided on said beam structure (50), said legs being provided with recesses (74) on the inner sides thereof providing a guiding function for the beam member.

13. The adapter as claimed in claim 10, comprising two vertical legs (82, 84) extending in a vertical direction from said attachment means (80), at the periphery thereof, the legs being provided with latches or hooks (86, 88) adapted to engage with the side walls of the beam structure of said femoral compression device.

14. The adapter as claimed in claim 13, comprising a support member (90) mounted at the periphery of the attachment means, opposite to where the legs are provided, and extending in the same vertical direction as the legs (82, 84), and being adapted to rest against the upper surface of the beam structure, thereby providing stability to the adapter means.

15. A method of controlled hemostasis at two puncture sites in each femoral artery or vein of a patient after catheterization, comprising:
 a) providing an essentially linear beam member having two pressure pads, adapted to bear against each puncture site;
 b) adjusting the center-to-center distance of said pressure pads by moving at least one of said pressure pads along said beam member;
 c) applying said pressure pads at said puncture sites;
 d) securing said beam member carrying said pressure pads to the body of said patient, by tightening a belt around the body.

16. The method of claim 11, wherein said beam member comprises attachment means for said pressure pads.

* * * * *